United States Patent
Neal (10) Patent No.: US 12,156,836 B1
(45) Date of Patent: Dec. 3, 2024

(54) CONTROLLED ACCESS COMPARTMENTED WHEELED CART

(71) Applicant: TAGCarts, Inc., Sacramento, CA (US)

(72) Inventor: Taggart Neal, El Dorado Hills, CA (US)

(73) Assignee: TAGCARTS, INC., El Dorado Hills, CA (US)

( * ) Notice: Subject to any disclaimer, the term of this patent is extended or adjusted under 35 U.S.C. 154(b) by 569 days.

(21) Appl. No.: 17/188,829

(22) Filed: Mar. 1, 2021

Related U.S. Application Data (60) Provisional application No. 62/982,606, filed on Feb. 27, 2020.

(51) Int. Cl.
*A61G 12/00* (2006.01)
*A47B 31/00* (2006.01)
*A61B 50/13* (2016.01)
*G06F 21/32* (2013.01)

(52) U.S. Cl.
CPC ............ *A61G 12/001* (2013.01); *A47B 31/00* (2013.01); *A61B 50/13* (2016.02); *A61G 12/008* (2013.01); *G06F 21/32* (2013.01); *A47B 2031/006* (2013.01)

(58) Field of Classification Search
CPC ... A47B 2031/006; A47B 31/00; A61B 50/13; A61G 12/001; A61G 12/008; B60B 33/063; G06F 21/32
USPC ...................................................... 312/348.3
See application file for complete search history.

(56) References Cited

U.S. PATENT DOCUMENTS

| 5,611,553 | A  | * | 3/1997 | Schoeman | ............. | A47B 46/00 280/47.35 |
| 11,166,559 | B1 | * | 11/2021 | Kadoch | .................... | B60B 33/04 |
| 2001/0035702 | A1 | * | 11/2001 | Murphy | ................ | A61B 50/10 312/285 |
| 2004/0104652 | A1 | * | 6/2004 | Holmes | ............... | E05B 65/0003 312/348.3 |
| 2005/0288571 | A1 | * | 12/2005 | Perkins | .................. | A61B 5/742 600/407 |

(Continued)

FOREIGN PATENT DOCUMENTS

| CN | 102727973 A | * | 10/2012 | ............ A61M 15/08 |
| CN | 208158162 U | * | 11/2018 | |

(Continued)

*Primary Examiner* — Matthew W Ing
(74) *Attorney, Agent, or Firm* — Heisler & Associates (57) ABSTRACT

A frame is carried upon wheels and also includes separate legs, with the wheels and legs movable vertically relative to each other so that the cart can rest upon the wheels or upon the legs. The cart includes multiple compartments, at least some of which feature secure access locks to limit access to authorized individuals. The compartments can be for storage or general items or for items which require a particular environment to be maintained. A display, preferably as part of a tablet, provides a video display for a user and also preferably provides at least one interface for controlling compartments, accessories and movement of the cart. Accessories can include medical functional equipment and aesthetic environment augmenting equipment. A power supply including a rechargeable battery is included with the cart, which in one embodiment can power the wheels for movement of the cart, such as between preset use locations.

6 Claims, 7 Drawing Sheets

(56) References Cited

U.S. PATENT DOCUMENTS

| | | | | |
|---|---|---|---|---|
| 2007/0244610 A1* | 10/2007 | Ozick | ............... | A47L 11/24 |
| | | | | 342/417 |
| 2008/0142612 A1* | 6/2008 | Potter | ............... | B05B 17/08 |
| | | | | 239/211 |
| 2014/0265182 A1* | 9/2014 | Stanton | ............ | A61B 6/035 |
| | | | | 280/30 |
| 2018/0008498 A1* | 1/2018 | Sciacchitano | ......... | E05B 65/44 |
| 2020/0078943 A1* | 3/2020 | Song | ............... | G05D 1/0214 |

FOREIGN PATENT DOCUMENTS

| | | | | |
|---|---|---|---|---|
| CN | 110664114 | A | * | 1/2020 |
| FR | 2570810 | A3 | * | 3/1986 |
| KR | 20160129390 | A | * | 11/2016 |

* cited by examiner

CONTROLLED ACCESS COMPARTMENTED WHEELED CART

CROSS-REFERENCE TO RELATED APPLICATIONS

This application claims benefit under Title 35, United States Code § 119(e) of United States Provisional Application No. 62/982,606 filed on Feb. 27, 2020.

FIELD OF THE INVENTION

The following invention relates to carts for carrying items on a wheeled frame. More particularly, this invention relates to carts which include powered accessories thereon and which carts can also take on the appearance of furniture, such as a nightstand, provided with accessories particularly useful at a bedside or chair side location and with multiple lockable compartments therein.

BACKGROUND OF THE INVENTION

Medical carts are known in the hospital environment and related patient treatment spaces. These medical carts come in a variety of different configurations, but generally include a frame supported upon wheels and configured to provide access to medical equipment, information management equipment, medications, and other items at various locations where the cart can be moved, with the carts configured to assist in various different medical related tasks. Some medical carts emphasize access to data and include a computer or other computing device, typically featuring a display and keyboard or other inputs, and often referred to as a "workstation on wheels" ("WOW"). Other medical carts are in the form of medication dispensing carts. Such medication dispensing carts typically include multiple different compartments which can contain different medications. Medical carts configured for medication dispensing can be configured to include locks of various different types so that access to medications contained therein is controlled. Such carts also include inventory management systems. Still other medical carts can be specialized for providing different therapies or performing different procedures, with the cart generally providing a mobile platform for the transport of various items of medical equipment and to support this medical equipment during use, such as within a patient's room within a hospital.

Many patients undergo various treatments while at home, or in a more residential environment, but still where procedures can be provided, such at skilled nursing facilities. Within such an environment, it is desirable to provide a more home-like atmosphere to enhance patient mental well-being and to provide an optimal experience for the patient or guest. When in such an environment, an individual (whether a patient or guest) will typically have other needs which are not medical in nature, but which can be simplified and made more convenient if provided through a cart-like interface. Such individuals often need some form of medical therapies to also be provided, which can be most optimally provided through a cart-like interface. However, in the prior art, storage for non-medical equipment and storage for medical equipment are typically kept separate. A need exists for a cart which can provide the benefits of a medical cart and also the benefits of non-medical item storage.

Within home environments, a variety of different forms of furniture are provided for storage of various different items. One known form of furniture is typically placed next to a bed, and is referred to as a "nightstand." Nightstands often include at least one cabinet and at least one drawer for containment of various different items. Nightstands also typically include a planar horizontal top surface upon which items can be rested. Items often rested upon a nightstand include lamps, clocks, and a variety of other items.

Typically nightstands are not configured to secure items contained therein, but rather typically items associated with the nightstand can be freely accessed. This can create problems for an individual user of such a nightstand, including risk of loss of privacy, theft of valuables, misuse of items associated with a nightstand, misplacement of items and other undesirable activities. Furthermore, many individuals, even if only capable of limited movement, migrate from a bedroom to a separate sitting area within a residence during the day (or at night).

One source of frustration is that such individuals with limited mobility often lose track of where various different items of importance to the individual are located. A need exists for a nightstand which can secure items from improper use, and which nightstand is mobile so that it can move with an individual, so that items contained therein and associated therewith are available at multiple locations within the residence. Such a piece of furniture would further benefit from having controlled access to compartments and/or drawers thereof and other equipment associated therewith, for the benefit of the individual. Such an item of furniture, could also be a platform for provision of various medical services within a home environment, such as for use in telemedicine, medication dispensing, and other provision of therapies.

SUMMARY OF THE INVENTION

With this invention, a wheeled cart is provided which is configured to appear as a piece of furniture, such as a nightstand, and which can contain various different items, at least some of which can be securely stored, and at least some of which can have a medical therapy character, while other items contained within the compartmented wheeled cart can be of a non-medical nature, but at least some of which benefit from having controlled access associated therewith.

One embodiment of this invention is disclosed in the included figure, and function thereof is illustrated by the included schematic. With regard to this embodiment, a frame is generally provided which is shown in this embodiment as generally orthorhombic in shape with a lower surface parallel with an opposite top surface, a pair of side surfaces parallel and opposite each other and a front and rear surface parallel and opposite each other, and with these pairs of surfaces generally mutually perpendicular to each other pair of surfaces. Other general shapes for the cart could alternatively be provided.

Most preferably, the lower surface includes feet extending down to near or full contact onto an underlying surface. By keeping the legs short, maximum space is provided for containment of items within various drawers and cabinets of the cart and height is minimized to be fairly close to bed height, as is the case with a nightstand. In one embodiment, feet on the bottom of the cart rest on the ground, unless wheels are extended down from the lower surface to lift the cart up onto the wheels and to allow for movement of the cart. In another embodiment, the wheels always remain in contact with the ground, and the feet merely look like they are in contact with the ground, but are actually elevated slightly. The wheels can be locked so that the cart has the appearance and stability similar to that of a regular nightstand or other similar furniture.

A front surface of the frame has a variety of accessible compartments. These compartments can include drawers or doors/cabinets. Generally, the drawers slide horizontally between a closed position and an open position, with the drawers being open (or including lids) on upper portions to access items contained within the various different drawers. The doors/cabinets generally are in the form of hinged doors which hinge about a vertical axis such that the doors pivot between being closed and being open. The drawers and doors can be manually actuated, or can be motorized for automatic control thereof. The entire cart can have a variety of different portions that can be reversible, such as for use adjacent to either a left side or right side of the bed.

Within compartments behind the doors, an open space can be provided, or alternatively shelves can be provided within at least some of the compartments. As a further alternative, various different sub-compartments such as sub-drawers or behind sub-doors can be provided within at least one of the compartments, with the sub-drawers taking up only a portion of the cabinet in which the sub-drawer is located, and with the door closing and concealing such an interior sub-drawer. The compartments can include at least some that are insulated and include a heat transfer subsystem so that the compartment maintains a lower temperature (refrigeration) or an elevated temperature (warming, such as for IV bags, blankets, ointments, topical solutions, etc.). Humidity levels can also be controlled in at least one compartment, such as with a humidor compartment.

Locks are associated with at least some of the compartments, whether they be drawers or doors. While these locks could be manual locks, such as padlocks or locks built into the drawer or cabinet, or a latch associated therewith, and which manual locks could be accessed through use of a key or by turning of dials to select a code, or pushing of buttons in a sequence, or other manual lock, most preferably these locks are electronic in nature and controlled by a CPU or other computer or computational system associated with the cart (or a tablet configured for use with the cart).

The CPU can implement a selective access protocol according to various different embodiments to allow for the locks to control who has access to the different compartments. Some compartments could be left unlocked. Other compartments would be locked in a manner that would only be accessible through entry of a master code (or entry of biometric information as described below). Other compartments might be accessible by an individual with a master code as well as accessible to individuals having lower levels of authority.

In one embodiment, each of the compartments can be accessed by an individual having a master code. Once such a master code is entered, access protocols can also be modified by interacting with the CPU and providing programming for the various different locks. In one embodiment, such a master code, such as a code associated with the primary individual utilizing the cart, allows for access to all of the compartments except for a medication compartment, and perhaps also some other selective access compartments. Such a medication compartment could have access thereto controlled by a medical professional remote from the cart (or near the location of the cart) especially for opioids, cannabis, or other controlled substances.

In one embodiment, a medication compartment can only be accessed once a certain amount of time has elapsed, and when a master code is entered by the user/individual. Otherwise, the medication compartment is not accessible. Medication compartments could be preloaded with medications that the individual is to take. Alarms could sound (or alarm lights flash), and information could be displayed instructing a user to take different medications at times when medication compartments have been unlocked and it is appropriate for the user to access the compartment to take the medications contained therein.

Various different items contained within the different compartments, whether they be drawers or cabinets, can generally include medication, nutritional supplements, sleep aids, sleep masks, vitamins, smoking articles, firearms, books, religious articles, sex toys and tools, other private items, magazines, puzzle books and puzzle items, personal hygiene items, food and a variety of other items which would benefit from being contained within the cart and accessible at a bedside or elsewhere when following the individual to another portion of a residence.

These various different items will be placed within different compartments based on who is to have access to the items. Then, the CPU or other computer system would have locks associated with each compartment programmed to provide selective access to the individuals that should have access to those compartments. In one embodiment, some compartments cannot be accessed unless two or more individuals enter their appropriate codes/keys, etc. to allow access to those compartments. In another embodiment, any one individual who has access according to the security protocol can open the appropriate compartment.

The cart also preferably includes various different elements/features associated therewith, which generally are provided either for physical health or mental health. One such item is a pulmonary health support system, such as an oxygen bottle, oxygen mask, oxygen tubing, and a bracket for supporting the bottle, mask and tubing in a specific location, such as directly adjacent to a side of the cart within reach of a bedside.

Another medical health system could include an intravenous fluid dispensing pole coupled to the cart. This pole (often called an "IV pole") could be extendable between different elevations, such as to enhance or diminished flow rate from an IV bag suspended from the pole. Tubing could also be attached to the pole and routable down to an individual or other patient for dispensing of IV fluids to the individual.

An essential oil or other aroma mister can be coupled to the cart as a further accessory and to enhance the atmosphere around the carts and/or provide therapeutic benefit. This vapor and mist dispenser would typically be further from the side of the cart adjacent to a bedside of the individual to enhance aroma within an entire room where the individual is located, rather than providing direct droplet therapy to the individual.

A water feature can be incorporated into the cart, such as resting upon the cart and also located typically on a portion of the cart most distant from the bedside of the individual. In this way, the water feature provides a visual and auditory desirable stimulus, but does not splash onto the individual or block surfaces which can be easily reached by the individual, and should remain available for placement of various portable items thereon.

Audio speakers are preferably provided which could be built into various different portions of the cart, or rest upon a top surface of the cart in various embodiments, or be affixed to an upper surface of the cart. In this embodiment, the speaker includes some buttons for control of volume thereon, and could also allow for tuning in radio stations, placement of removable media containing sound files, such as audiobooks or music, and which also could act as ports for attachment of charging accessories, such as USB ports which can allow for powering (and data transmission) with smartphones and other portable electronic devices.

The cart preferably includes a call button in an easy to reach location from a bedside for an individual. One such location would be an upper front edge of the cart, with the button perhaps colored a bright color and extending away from the surface of the cart sufficient that even a blind or sight impaired individual could still easily find this call button and push a button thereon. This call button could be associated with a local alarm to notify attendants in other rooms of the facility, or could be coupled to remote alarm systems, such as the 911 emergency system, in various embodiments.

A display is preferably provided on the cart to enable a variety of different functionalities. The display can be part of a tablet computing device (such as those provided under the trademark "iPad" by Apple, Inc. of Cupertino, CA) or the display can be directly drawn by a CPU on the cart. This display can be utilized (especially if it is a touch screen) in programming the overall cart and lock systems and other features of the cart in one embodiment. This display can also be provided for broadcasting of entertainment. This display can also be utilized such as in telemedicine and for interacting with the individual. Various biomedical sensors can be provided and incorporated into such a telemedicine session as well, such as pulse level sensors, blood oxygen sensors, blood pressure sensors, blood analysis sensors (e.g. blood glucose testers), etc. This display preferably faces a bedside of the individual from the cart from a side surface, so that the user/individual can merely roll onto the individual's side, or the individual can turn the individual's head toward the cart, and view the display.

Images on the display can be rotated in one embodiment, so that an upper portion of the image is at the right and the lower portion of the images at the left, so the images appear to be upright even when a patient is lying down and viewing the display. A microphone and camera can be associated with the display or otherwise associated with the cart, so that sound and visual input can be inputted at the cart.

In one embodiment, the CPU or other computer or processor is configured to operate based on voice recognition technology to enable various different subsystems of the cart based on voice commands alone. The display can be in the form of a touchscreen, so that an individual can further interact with the various different subsystems through the display by touching appropriate areas on the display. Other buttons, such as a keyboard could be provided through the display or on a separate portion of the cart.

The various different subsystems of the cart, including the pulmonary support systems. IV and circulatory support systems, speaker, display, oil/aroma mister, humidifier (or dehumidifier), water feature, and any other accessories can each be considered as accessories within an overall system of this invention. This overall system of this invention also includes the various different compartments, such as in the form of drawers or cabinets, and with a lock associated with each compartment.

Other portions of the overall system include the display and potentially biometrics to verify access to the various different subsystems of the invention. Other parts of the overall system can include a transmitter/receiver for wireless communication with the Internet or other local wireless transmitter/receivers associated with other systems, as well as the power supply, optionally including a battery, and various sensors. Details of these various different parts are described in detail below.

Biometrics can be associated with the display, such as a camera on the display which can provide facial recognition, or a thumbprint scanner or fingerprint scanner either associated with the display or elsewhere on the cart, and reading fingerprints for authorization of access. Other forms of biometrics could include retina scanners, voice recognition scanners associated with a microphone, or other biometric access restriction systems linked into the CPU and other systems of this invention, whether the biometrics are part of the display or separate from the display.

The transmitter/receiver could be in the form of radio frequency wireless transmissions, such as those provided under various protocols, such as Bluetooth protocols, Wi-Fi protocols, cellular protocols, UHF radio, VHF radio, HF radio, 5G or other frequencies/protocols, or other wireless transmission and reception protocols. This transmitter/receiver would generally be tied into the CPU to provide for input and output of signals relative to the CPU and for further processing and distribution to other subsystems of this invention, such as for communication with other systems remote to the cart, and/or for reception of a video signal and presentation of that video signal on the display.

The power supply can, in a simplest form of this invention, be a power cord which plugs into wall power and includes a transformer to convert the power to DC power for powering the CPU. A portion of this power supply could remain in an AC format, such as to power AC pumps, motors or other equipment associated with various different accessories and subsystems up on the cart. DC power can also be provided through a transformer to power various different sub systems and accessories associated with the cart.

In one embodiment, a battery is provided which is recharged by the power supply, and supplies DC power (or AC power through an inverter) to various different subsystems and accessories associated with the cart. In one embodiment, this onboard power supply is sufficient to power a defibrillator. Most preferably, the battery and power supply are both located at a lower most and rear portion of the cart, to enhance stability of the cart by having the weight of these items located on a lower portion of the cart. In one embodiment, the power supply can supply power to wheels so that the cart can be moved other than by pushing manually. The wheels could also be rotated by servo motors so that they can steer the cart, and the cart can be moved by remote control or autonomously.

The CPU can include and or interact with separate components including a clock, memory, different inputs into the CPU and different outputs out of the CPU. These inputs can include sensors. Sensors can be associated with each of the compartments and with each of the accessories in one embodiment. These sensors can provide status information to inform an individual and/or the CPU as to the status of the various different compartments and accessories, such as if they are open or closed, locked or unlocked, on or off, etc.

These sensors can also be provided as a portion of various different feedback loops for automated control of the various different accessories and subsystems of this invention. As an example, sensors on the oxygen bottle can indicate when the oxygen bottle is empty or about to become empty, and a control system can interact with this sensor to cause a notification to be sent that oxygen is running low, and so that further oxygen can be supplied. Similarly, other sensors associated with different accessories and subsystems can operate within appropriately programmed feedback loops to provide automated control and optimal performance for the different subsystems associated with the cart.

Other accessories not shown but also providable with the cart of this invention can include reading lights, wireless systems to project video images from the display on the cart to a separate display, such as a television set, within the room where the cart is located. These accessories can facilitate telemedicine sessions through the microphone, a camera and the display on the cart, or through other equipment within the room where the cart is located.

In one embodiment, at least some of the compartments are configured to maintain a specialty temperature, such as refrigeration, or heated to an elevated temperature. Control of heating and cooling systems can be provided through appropriate sensors and other control systems to maintain desired temperature for these compartments. Such compartments could contain food, medications, warm towels or wraps, ice and/or various other items at distinct desired temperatures. These heated and cooled compartments could be locked or unlocked depending on the desires of users of the cart.

In one embodiment, smartphone/smart tablet application software (also known as "apps" could be provided along with the cart. Control of various aspects of the cart could be controlled through the app. For instance, access restrictions to different compartments of the cart could be controlled through the app. Furthermore, audit capabilities could be integrated between such an app and the cart. The CPU and memory onboard the cart could run a cart operating system which also facilitates such auditing capabilities and control, through a cart interface and/or through such an app. In one embodiment, the cart CPU and systems would only be controllable through such an app operating on a smartphone or smart tablet. In other embodiments, the display and interfaces on the cart would also allow for interaction with the cart.

Various examples of how such audit capabilities could be integrated into such an operating system on the cart, either including control through a separate app or otherwise, include having one drawer, such as a religious health/Bible drawer containing religious literature, such as a Bible. Information would be gathered such as how often that drawer is opened, how long that drawer remains open, whether the drawer contains the Bible or not when the drawer is closed, frequency and/or times that the drawer is open, etc. In another example, a "life couple" app example would know how often the couple utilized "dual" credentialed access to sexual health drawer together, perhaps, tracking over time, alerts, etc. to provide feedback and useful analysis. In another example involving an app such as "WebMD" or some other similar app, medical professionals could have access to how often such medical information apps are accessed, and what questions are being asked, so that healthcare to an individual associated with the cart could be optimized, such as by providing controlled access to various different drawers such as medication drawers, nutritional supplement drawers, herb drawers, etc., to facilitate optimal patient health.

The CPU and associated cart operating system could implement an inventory management system. In some embodiments, inventory management may be utilized through RFID or other technology (e.g. barcodes) so that items are reconciled and PAR levels managed, monitored or maintained relative to a number of door "closes." The system would thus "know" that an item such as a pain relief pill had a certain number of units when the drawer was last opened and should have a certain lesser (e.g. one less) number of units when that drawer is later closed.

Items may be RFID tagged individually so that RFID scan reveals what may or may not be missing upon conducting reconciliation cycles. Restocking of drawers or other compartments on the cart could thus be scheduled for efficiency. Automatic renewal of prescriptions could be initiated by such systems. Orders can be placed through appropriate retail channels, including delivery channels for delivery of items to restock the cart in a semi-autonomous or fully autonomous fashion.

Furthermore, such inventory management would allow for remediation in situations where recalls have occurred. Such inventory information could be aggregated, such as in an anonymous manner, to provide valuable feedback to drug producers that more drugs need to be manufactured, or, for other items, to provide valuable feedback as to which different items are being consumed, either to feedback into production systems, or to trigger other marketing or production efforts or other strategic planning by suppliers of items handled by the cart.

OBJECTS OF THE INVENTION

Accordingly, a primary object of the present invention is to provide a location for storage of different types of items with at least some degree of concealment and/or secure access, which location can be carried upon a wheeled frame to allow for movement between different locations and to provide access to the different items at multiple locations.

Another object of the present invention is to have this location, which functions as a cart, have the appearance of stationary furniture, such as a bedside or chair side stand.

Another object of the present invention is to provide a medical cart which has the appearance of a nightstand or chair side stand, or similar piece of furniture.

Another object of the present invention is to provide a wheeled frame with compartments for various different items, which wheeled frame also includes legs thereon separate from the wheels, and which legs and wheels can be adjusted vertically so that the frame can rest either upon the wheels or can rest upon the legs.

Another object of the present invention is to provide a power supply for powered items upon a wheeled platform which power supply can operate both when plugged into a source of power and when not plugged into a source of power, utilizing an onboard battery.

Another object of the present invention is to provide a grouping of controlled access compartments which are carried on a mobile frame and can be accessed at multiple different locations.

Another object of the present invention is to provide compartments upon a frame which have different secure access protocols, with some compartments requiring authorization for access from a remotely located medical provider, and with other compartments having controlled access granted to a user at a location of the compartments.

Another object to the present invention is to provide a multi-compartment wheeled frame with controlled access to compartments thereof, which frame can autonomously move between different locations, such as to remain in proximity with a user.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 (FIG. 1) is directed to a cart which in this embodiment has the appearance of a nightstand or chair stand, so that the functionality of a medical cart can be brought into a home environment (FIGS. 4, 5 and 7) without disturbing ambiance and maintaining a home-like setting. The cart 10 can be utilized for support of medical accessories and ongoing medical treatment, and can also be utilized more for general convenience and support of an individual with or without any physical impairment.

Figure 1:
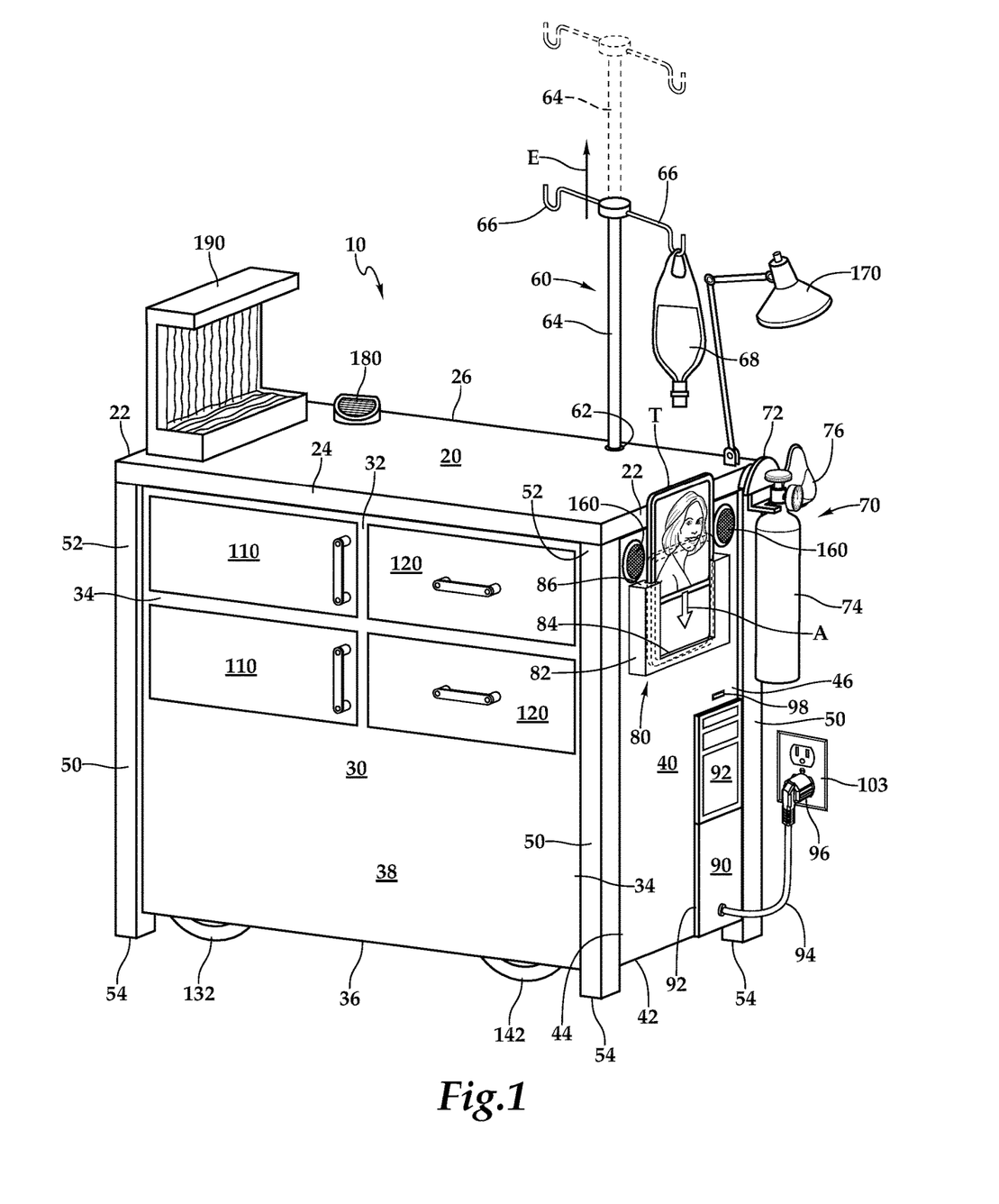
FIG. 1 is a perspective view of a cart according to one embodiment of this invention, shown plugged into a source of power and with a variety of compartments and accessories associated therewith.

In essence, and with particular reference to FIG. 1, basic details of the cart 10 of this invention are described, according to an example embodiment. The cart 10 has compartments and accessories carried upon a wheeled frame. An exterior of this frame of the cart includes a top surface 20, a front surface 30 and a side surface 40 which are visible in FIG. 1. The top surface 20 includes various accessories thereon and preserves a large open space for placing of various items and can act as a workspace, dining space, etc. The front surface 30 provides access to compartments within the cart 10, and with the compartments generally configured to give the cart 10 the appearance of a nightstand, bed stand or a chair side stand. The side surface 40 defines a side of the cart 10 facing a bed B or chair C and can support various accessories which benefit from facing and otherwise being closest to a user resting upon the bed B or sitting upon the chair C.

The cart 10 includes legs 50 at corners thereof. The cart can rest upon these legs 50 or can be elevated (along arrow G of FIG. 2) so that the cart 10 rests upon and can move upon wheels 132, 142. Accessories on the top surface 20 include an IV pole 60, a lamp 170, an aroma generator 180, a water feature 190 and potentially other accessories. The side surface 40 can support an oxygen system 70 and tablet T support 80 in an orientation and location which facilitates ease of use for the user while in the bed B or a chair C. Speakers 160 can also be provided, such as in the side surface 40.

Figure 2:
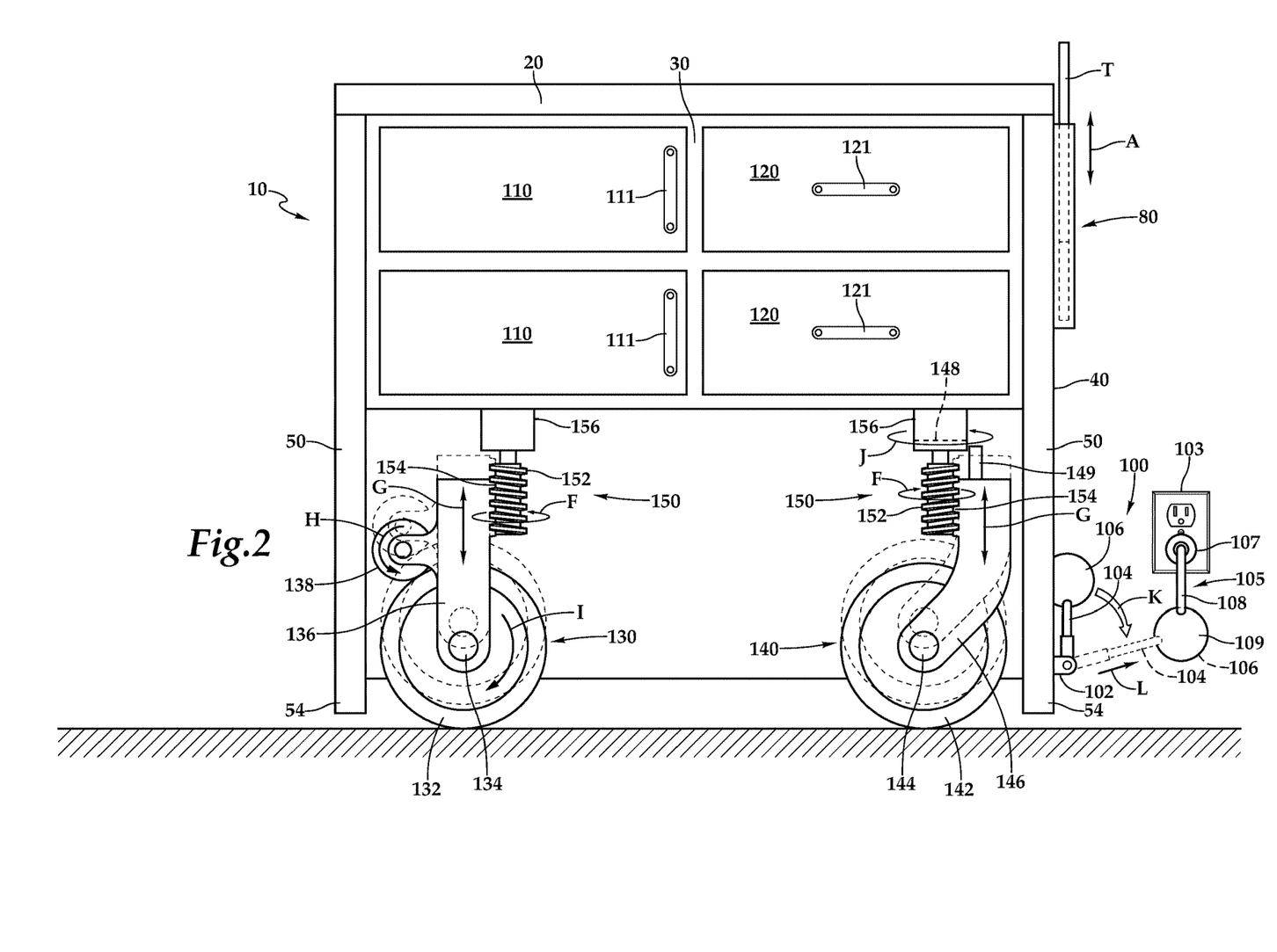
FIG. 2 is a front elevation view of that which is shown in FIG. 1, and showing the cart carried above ground on its wheels, and with legs thereof above ground, and also utilizing a wireless power connection to an electrical wall outlet through a wireless charging accessory plugged into the wall outlet.

A power supply 90 is built into the cart 10, and in this embodiment has portions thereof accessible through the side surface 40, including for plugging into a wall outlet 103 or utilization of a wireless charging system 100 (FIG. 2). The front surface 30 of the cart 10 features doors 110 and drawers 120. In this embodiment, the doors 110 and drawers 120 act as exterior compartment access structures which, when opened, provide access to sub-doors 112 and/or sub-drawers 115 which preferably have limited access controlled by lock buttons 114, 118 and/or through electronic locks built into these compartments. Locks can be controllable remotely, through the tablet T or otherwise, and with access limited according to access limitation protocols suitable for each particular compartment.

The wheels 132, 142 in this particular embodiment are coupled to either a driven wheel assembly 130 or a steered wheel assembly 140 (FIGS. 2 and 3) as well as a wheel lift assembly 150. A driven wheel assembly 130 provides for powering of at least one wheel of the cart 10 for movement of the cart 10 in a powered and optionally automatic fashion. The steering wheel assembly 140 provides for steering of at least one wheel so that the cart 10 can be pivoted, turned and navigated while moving in an at least partially autonomous fashion. The wheel lift assembly 150 allows for raising and lowering of the wheels 132, 142 relative to a height of the legs 50, so that the cart 10 is either resting upon the legs 50 or upon the wheels 132, 142 (or both). As an alternative, or in addition, the legs 50 can be caused to telescope or otherwise move vertically to provide relative height adjustment between the legs 50 and the wheels 132, 142.

Control system 200 includes a CPU which is coupled to a variety of different sensors, compartments, locks, accessories, the display/tablet T and power supply 90. This control system 200 manages controlled access to the compartments, manages operation of the various accessories of the cart, logs activity associated with the cart, manages telemedicine sessions along with the tablet T, monitors power usage, controls motion of the cart 10, such as to follow the user between various different locations (such as a bedroom and a sitting room shown in FIG. 7) and provides various other functions, either alone or in conjunction with software operating within a processor and/or memory of the tablet T, for coordination of operation of the cart 10 and tablet T together.

More specifically, and with continuing reference to FIG. 1, details of the top surface 20, front surface 30, side surface 40 and legs 50 are provided, according to this example embodiment. In this embodiment, the cart 10 is configured to appear like a piece of furniture with the wheels 132, 142 largely or totally hidden and with the cart 10 resting upon feet 54 opposite upper end 52 of the legs 50. The legs 50 are provided extending vertically at corners of the cart 10, extending all the way up to the top surface 20.

While these legs 50 are shown as static, the feet 54 could telescope within (or relative to) other portions of the legs 50 to allow for height adjustability within the legs 50 themselves. As one example, the feet 54 could be at a lower end of a square cross-section vertically elongate structure nested inside of a larger square cross-section of each leg 50, with the larger cross-section of each leg 50 defining an exterior surrounding a hollow interior chamber. The feet 54 and associated structure could move vertically relative to outer portions of the legs 50.

Actuation of such movable feet 54 could be by a screw jack, pneumatics, hydraulics, an electric motor, and/or various gear drive mechanisms. Control of height of the legs 50 would be provided through the CPU of the control system 200, and/or optionally at least partially through programming on the tablet T. The tablet T can interact with the cart 10 through a wired or wireless (e.g. Bluetooth) communication protocol.

While the legs 50 are shown visible at the corners, they could be hidden within an exterior of the car at 10. Legs 50 are shown standing vertically, but could taper somewhat, such as to achieve aesthetic goals, and generally to cause the cart 10 to look as much like furniture and as little like a medical cart as possible. Such aesthetic is desirable to conceal that an individual is in need of sophisticated medical support, and to provide a peaceful and homey atmosphere for the user/patient, whether at home, in an acute care hospital or similar setting, or in a retirement home or skilled nursing facility. In some embodiments, the cart 10 is provided less for medical care and more for controlling secure access to different compartments therein, primarily by user, so that it is further desirable to have the appearance of common furniture, rather than merely a frame supporting multiple lockable compartments on wheels.

The top surface 20 is preferably a rigid planar surface which supports various accessories thereon and is located at an upper end of the legs 50. This top surface 20 is generally located at and defines an upper portion of the cart 10 and is at a height similar to that of bedside and chair side furniture, such as about 25 to 35 inches in height above ground. The top surface 20 extends between side edges 22 which are preferably parallel to each other and defining a width of the top surface 20. The top surface 20 also extends between a front edge 24 and a rear edge 26, generally defining a depth of the top surface 20. Typically, the width of the top surface 20 is greater than the depth of the top surface 20, but such a proportion could be altered. The top surface 20 can be a gaming surface, such as featuring touchscreen digital glass for chess or other gaming display and control. The top surface 20 can be recessed somewhat as it extends away from edges 22, 24, 26 to resist spills migrating off of the top surface. Accessory locations and holes can also optionally be raised and/or sealed to prevent leaking or liquid contact damage.

While the top surface 20 provides various accessories thereon, the top surface 20 also preferably includes a large space which is not occupied, so that free space is provided for temporary laying down of items and performing of various tasks which benefit from having a rigid horizontal surface. Accessories on the top surface 20 can be affixed thereto or can conceivably be removably attachable thereto, either by merely placement on the top surface 20, or through utilization of clamps, adhesives, or other fasteners. The top surface 20 (and optionally other surfaces and structures) can be inherently anti-microbial in nature, or modified to present anti-microbial contact surfaces to the user. Most preferably, the top surface 20 is formed of hardwood material similar to that which furniture is often formed of, to provide the desired aesthetic. Stone would be another option. This hardwood appearance would typically include visible wood grain, but could be painted. A wooden appearance could be restricted to a thin veneer or form the entire thickness of the top surface 20.

A front surface 30 defines a forward facing portion of a frame of the cart 10. This front surface 30 is typically approximately within a single vertical plane, but could be in non-vertical orientation and could be non-planar. Such a variation can allow the cart 10 to take on an appearance similar to that of a variety of different types of furniture. The front surface 30 includes a top edge 32 adjacent to the top surface 20 and two lateral edges 34 defining sides of the front surface 30. Bottom edge 36 preferably extends down near to underlying ground to define a skirt 38 which can partially or entirely conceal wheels 132, 142 on a lower portion of the cart 10. While this skirt 38 is shown as planar in form, and with the bottom edge 36 being straight, the bottom edge 36 could be non-linear, such as lower near one end thereof and higher at a midpoint, and still conceal the wheels 132, 142. The front surface 30 is also preferably formed of hardwood or otherwise having a wood grain appearance similar to that of typical furniture. A primary function of the front surface 30 is to provide access to various compartments associated with the cart 10, as described in detail below.

Figure 4:
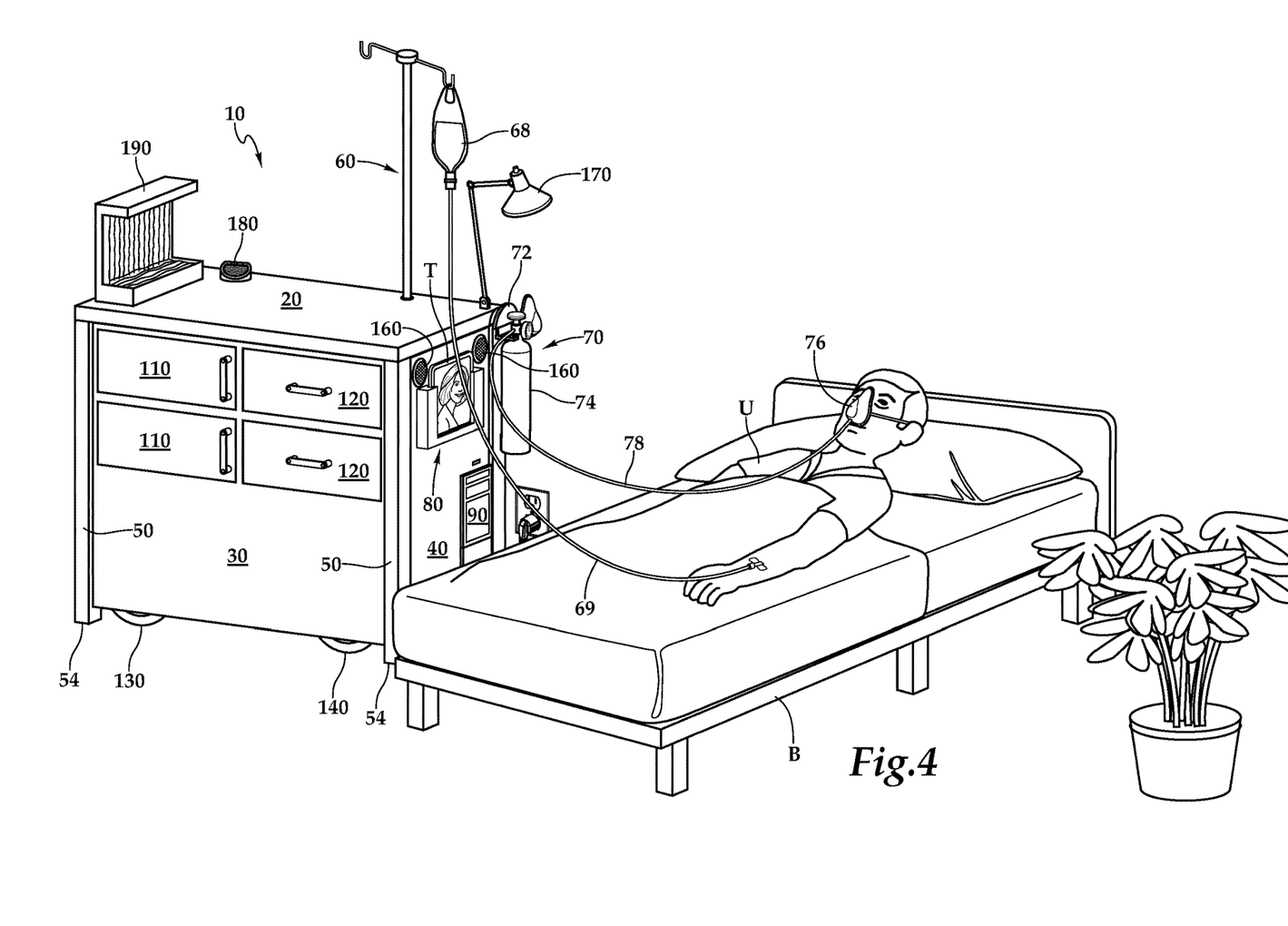
FIG. 4 is a perspective view of a bedroom scene with the cart of FIG. 1 shown in use at a bedside location.
Figure 5:
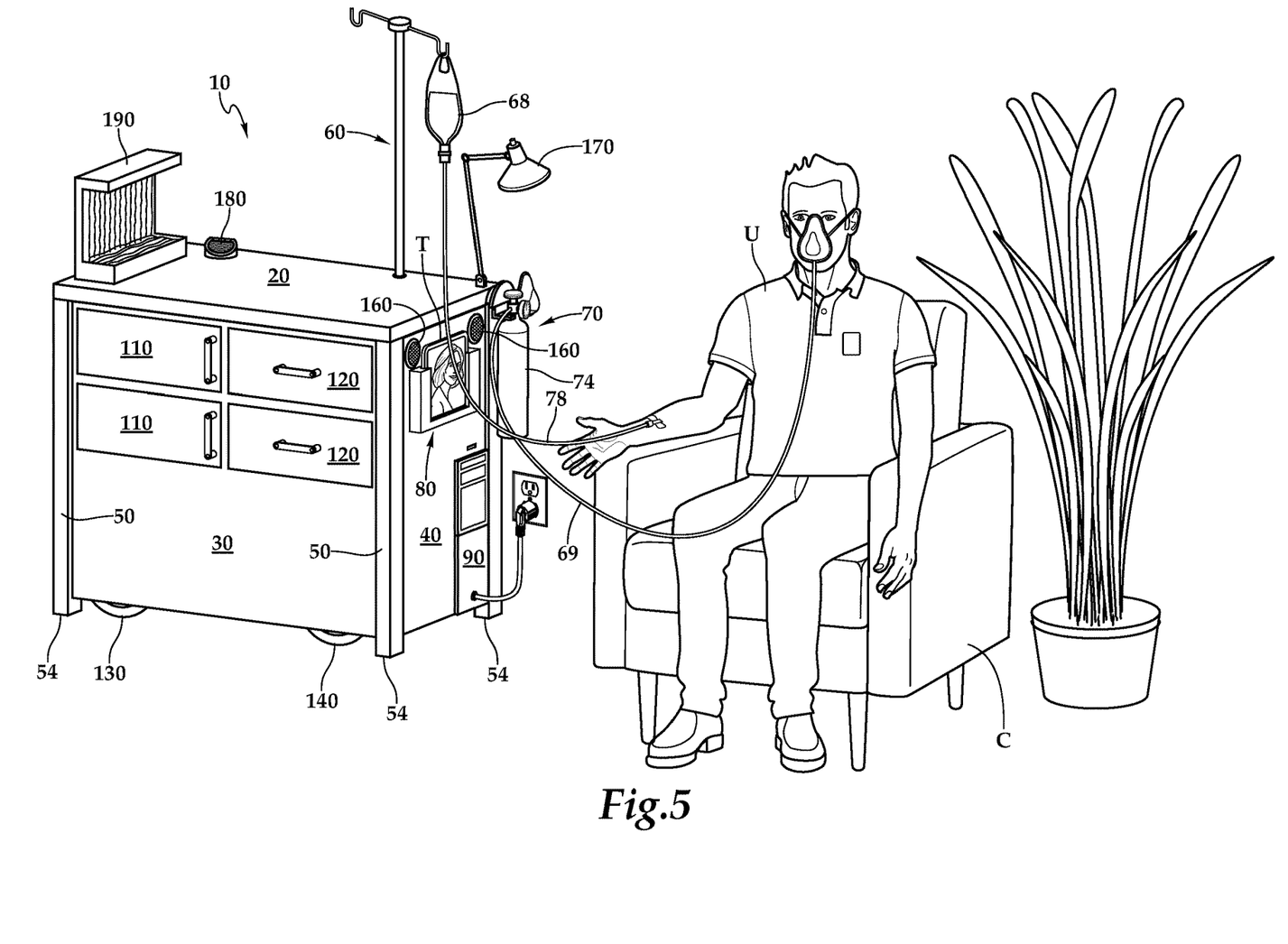
FIG. 5 is a perspective view of a sitting room scene with the cart of FIG. 1 shown in use at a chair side location.

The side surface 40 defines one side of the cart 10 closest to a bed B or chair C (FIGS. 4 and 5). This side surface 40 can be configured to support accessories and items which benefit from facing the user while the user is resting in the bed B or sitting within the chair C. The side surface 40 is typically vertical and planar extending between a lower edge 42 and an upper edge adjacent to the top surface 20. A forward edge 44 is adjacent to the front surface 30. A rearward edge 46 is opposite forward edge 44. The side surface 40 could be non-planar and/or non-vertical in various embodiments, such as to give the cart 10 the appearance of a non-mobile piece of furniture, such as a nightstand. The side surface 40 can also be provided of hardwood or with an exposed grain appearance generally similar to that of hardwood or other wood grain appearance, to further give the cart 10 an appearance of ordinary furniture. The accessories associated with the side surface 40 are described in detail below. The various surfaces 20, 30, 40 can be at least partially clear to allow viewing of contents of the cart 10 in various specific locations.

With particular reference to FIG. 1, as well as to FIGS. 4 and 5, details of an intravenous (IV) pole 60 accessory of the cart 10 are described, according to this example embodiment. The IV pole 60 is provided as an optional accessory for the cart 10 to allow an IV bag 68 to hang from a hanger 66 at an upper end of a shaft 64 of the IV pole 60. The shaft 64 extends through a support hole 62 formed in the top surface 20 for support of the IV pole 60. As an alternative, the shaft 64 could be secured to a rear side of the cart 10 adjacent to the rear edge 26 of the top surface 20.

While the IV pole 60 could have a variety of different positions, preferably it is somewhat closer to the side surface 40 to allow for convenient access to the user. As shown in FIGS. 4 and 5, if the user is receiving an infusion from the IV bag, a line 69 extends from the bag 68 and flows, typically by gravity (but optionally with support of a pump) through a catheter accessing the body of the user.

Most preferably, the IV pole 60 can be adjusted in height. For instance, the IV pole 60 might be collapsible down sufficiently that the hangers 66 are adjacent to (or even conceivably hidden behind) the top surface 20. When the IV pole 60 is needed, it can be extended vertically (along arrow E of FIG. 1) to provide appropriate gravity flow of fluids from the IV bag 68, along the line 69 to the patient.

In one embodiment, raising and lowering of the shaft 64 can be automatically controlled through the tablet T or remotely, such as by medical professionals and through a telemedicine interface with the cart 10. As one example, if biometric data indicates that the user/patient needs a higher rate of infusion, the IV pole 60 might be raised to a higher elevation so that elevation difference would be increased and flow rate from the IV bag 68 would also increase.

By placing the IV pole 60 near the rear edge 26 of the top surface 20, the primary portion of the top surface 20 is not blocked by the IV pole 60 from a front of the top surface 20, so that access to the top surface 20 is not inhibited by the presence of the IV pole 60. However, in alternative embodiments, the IV pole 60 could be at various different locations on the cart 10. The IV pole 60 can be removable in one embodiment, so that users who do not require the IV pole 60 can have it eliminated, and if users need an IV pole 60 which is not present, such an accessory can be added to the cart 10.

With particular reference to FIGS. 1, 4 and 5, details of the oxygen system 70 are described, according to this example embodiment. The oxygen system 70 is an optional accessory to allow the cart 10 to support medical needs of a user U which requires or benefits from supplemental oxygen therapy. The oxygen system 70 generally includes a bottle support bracket 72 at an upper end of the side surface 40 or affixed to the side edge 22 of the top surface 20 adjacent to the side surface 40. This bottle support bracket 72 preferably supports an upper end of an oxygen tank 74. A mask 76 can rest upon an upper portion of a tank 74 or an upper portion of the bottle support bracket 72 when not in use. Otherwise, the mask 76 can be worn by the user U. Tubing 78 can extend from the tank 72 (and particularly a regulator in an upper end of the tank 74) and lead to the mask 76 when the oxygen system 70 is in use.

Typically a regulator and an upper end of the tank 74 can be manually rotated to control flow of oxygen therefrom. As an alternative, the cart 10 can be configured to regulate flow of oxygen 70, and such oxygen flow can be measured by sensors associated with the cart 10, so that an amount of oxygen being delivered to the user U can be monitored by the cart 10, such as for sharing with medical personnel through a telemedicine visit, or otherwise through communication between the cart 10 and a medical professional at a remote location (or optionally a medical professional at the same location as the user U). Furthermore, an amount of oxygen remaining within the tank 74 can be monitored manually through visualization of a gauge on the tank 74, and/or can be coordinated with a sensor on the cart 10 so that an amount of oxygen within the tank 74 can be monitored remotely, such as by medical personnel or by a medical oxygen supply company tasked with keeping the user U properly stocked with oxygen.

Various advanced algorithms can optionally be provided to optimize utilization of the oxygen system 70, in various embodiments. For instance, the user U can be instructed, such as by speakers on the tablet T or text commands appearing on a display of the tablet T (or by separate speakers 160 mounted to the cart 10) for the user U to face the tablet T and an associated forward facing camera on the tablet T. Software akin to that of facial recognition software can then study the face and head of the user U and identify whether the mask 76 is being worn, and potentially also to some extent how properly the mask 76 is being worn. The system, through the tablet T, can instruct the user U to turn from side to side, so that side views of the mask 76 can be viewed, if desired. Such mask 76 utilization can be verified periodically, either through promptings to the user U, or passively with the cart 10 periodically visualizing the user U. If the system detects improper mask 76 wearing, the user U can be instructed to improve mask wearing particulars. If compliance is not forthcoming, communication to support individuals either located with the user U are the remote location, can be notified.

Furthermore, if the mask 76 is not being worn at all, the oxygen flow can be shut off by such a system, such as to preserve oxygen supply. The oxygen system 70 can optionally include other sensors such as a pulse oxygen sensor which is often configured to be attached to a finger of a user. The user U could wear such a pulse oxygen sensor continuously, or be periodically asked to insert a finger into a pulse oxygen sensor on the cart 10, for monitoring of oxygen levels of the patient. If oxygen levels outside of desired parameters are detected, rates of oxygen flow can be adjusted. If the user U has adequate oxygen levels at very low oxygen supply rates, and if otherwise medically indicated, the user U can be invited to remove the mask 76 and the oxygen system 70 can be shut off. Medical personnel can monitor the user U and provide appropriate interventions to keep the user U in a state having adequate oxygen levels through such an oxygen system 70, with either a greater amount of human intervention or a greater amount of automation, depending on the particular circumstances and goals.

Figure 3:
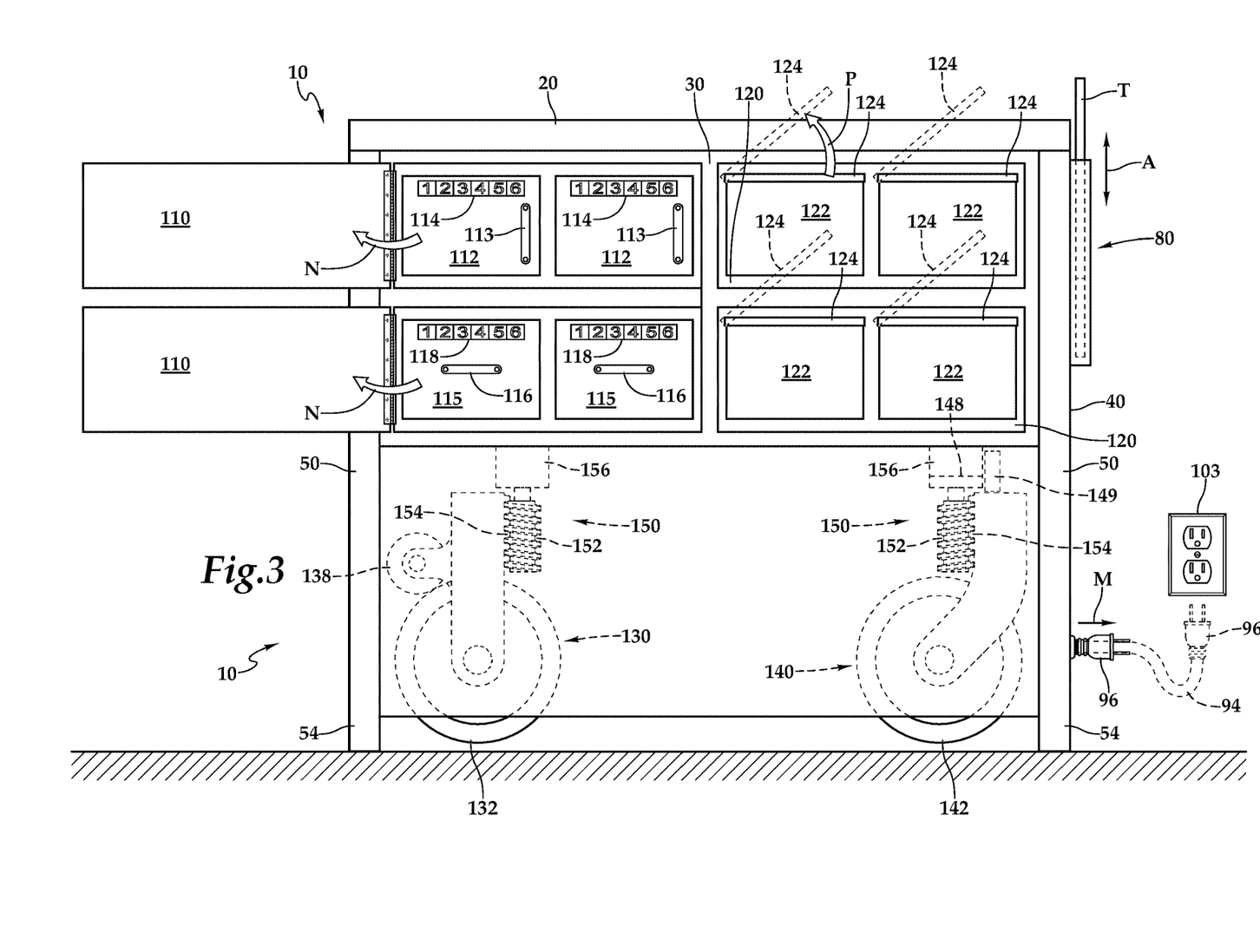
FIG. 3 is a front elevation view similar to that which is shown in FIG. 1, but with doors and drawers of the cart shown at least partially open, and with the wheels retracted so that the cart is resting upon feet at the bottom of legs thereof.

With continuing reference to FIGS. 1, 4 and 5, as well as FIGS. 2 and 3, details of a tablet T support 80 are described, according to this example embodiment. The purpose of the tablet T support 80 is to allow the tablet T to be held in a desirable position and orientation for use by a user U who is resting in a bed B or sitting in a chair C near the cart 10. This orientation is generally preferably within a vertical "portrait" orientation and near an upper end of the side surface 40 facing the user U. Most preferably, the support 80 allows the tablet T to be moved up and down somewhat, for optimization of viewing angle, and also to allow for more secure storing when not in use, and also potentially to facilitate charging (such as by movement along arrow I FIGS. 1-3).

In one embodiment, the support 80 include side brackets 82 spaced apart by a distance similar to a width of the tablet T. and including side flanges and front flanges at a 90° angle to each other and surrounding a gap adjacent to the side surface 40 having a thickness similar to the thickness of the tablet T. A bottom bracket 84 defines a lower portion of the support 80 adjacent to lower end of the side brackets 82. The bottom bracket 84 keeps the tablet T from falling down to the ground, and out of the side brackets 82.

Resilient friction surfaces 86 can be provided on portions of the brackets 82, 84 which come in contact with the tablet T. Thus, elevated friction is provided and the tablet T can be held in position at various different locations either totally within the side brackets 82 and against the bottom bracket 84, or elevated somewhat above the bottom rack at 84. Other forms of height adjustment can alternatively be provided if desired. Also, the brackets can be configured upon a common horizontal rotating axle, pivotable mounted to the cart 10, or a magnet on the brackets allowing for depositing relative to the side surface 40, to allow customized rotation and/or position of the tablet T to match an angle of the head of the user U.

In one embodiment, the bottom bracket 84 is configured with a power supplying plug compatible with a power port on the tablet T. For instance, a USB port on the tablet T of some known configuration, or a configuration developed in the future, can have a compatible plug built into the bottom of the bracket 84 at the location of which aligns with the port on the tablet T. When the tablet T is inserted all the way down against the bottom bracket 84, the tablet power port engages with the plug so that recharging of the tablet T can occur. Such a port could optionally also provide transmission of data signals between the cart 10 and the tablet T.

As an alternative, wireless charging could be built into portions of the support 80 or the side surface 40 (or could be provided built into portions of the top surface 20) so that wireless charging of the tablet T can be facilitated, or to allow for wireless charging of a smart phone or other accessory which is configured for wireless charging (such as charging which results from inductive coupling and is often referred to as "Qi" charging).

The cart 10 preferably includes speakers 160 built thereinto. The speakers 160 can be in the form of Bluetooth speakers which communicate with the tablet T and can provide a higher range of volumes than would typically be provided by the tablet T itself through onboard speakers. However, the system of this invention could be implemented entirely through speakers built into the tablet T or could operate without audible features, such as through provision of readable text on a display of the tablet T. The speakers 160 could be configured as "smart speakers" that provide various services, such as tuning in radio or internet audio programming, such as with voice commands or manual controls on or near the speakers 160. A larger bass speaker can be embedded within the cart 10, especially at a lower fixed or movable location for ballast control.

Figure 6:
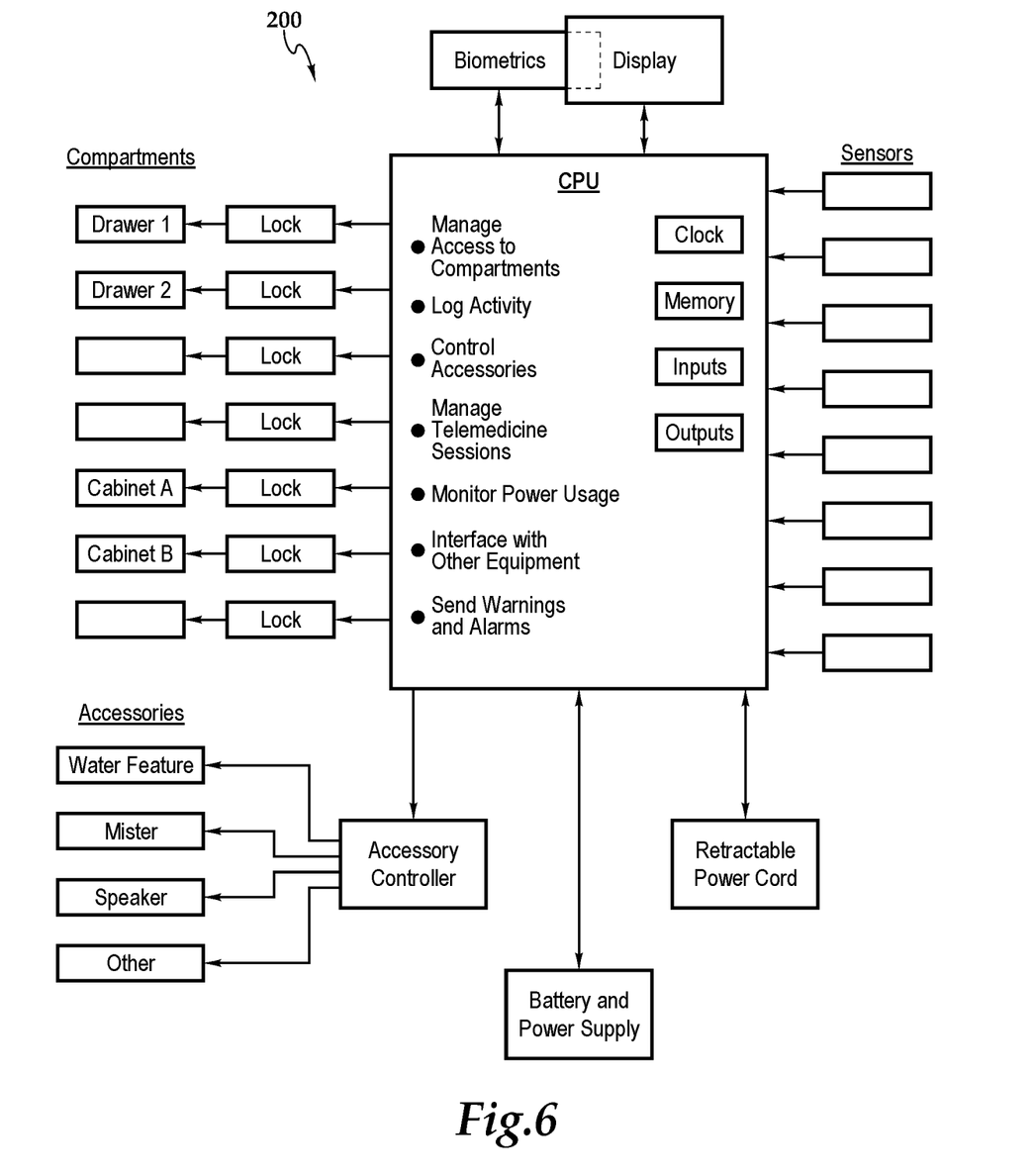
FIG. 6 is a schematic depicting interactions between a computer or other control system and various sensors and compartments and accessories and a tablet or other display to control function and/or movement of the cart.

While the tablet T is provided in a preferred environment of this invention, and the tablet T is removable so that it can function with the cart 10, even while in the hands of the user U, the tablet T and functions associated therewith could be built into the cart 10 in a permanent fashion. In such an embodiment, the tablet T shown in the figures would merely be replaced with a display and processing portions of the tablet T would have their tasks performed by a CPU built into the cart 10 (FIG. 6). The display could be a touchscreen or other input devices could be provided.

Various different functions of the cart 10 can be controlled through software or hardware and the software and/or hardware could be on the cart 10 itself, such as within the control system 200 (FIG. 6) or within the tablet T. Most preferably, function of the cart 10 is provided through a mixture of software operating within apps on the tablet T and software and hardware built into the cart 10 (and also remotely running software and hardware).

The tablet T and/or cart 10 include communication capabilities to allow for communication into a location spaced from the cart 10, either at a room nearby, or conceivably at any other location. Options for such communication can include cellular data, as well as voice telephone signals, through telecommunications hardware either built into the tablet T or built into the cart 10 (or both). As another option, the cart 10 can have a Wi-Fi antenna which works with a Wi-Fi base station which base station has communication access either to a local area network, such as within a care facility, or out to the Internet. Services such as telemedicine services can be provided from individuals at remote locations which themselves have access to the Internet. As a further alternative, a cart 10 and/or tablet T could be paired with a device such as a smart phone, which smart device has access to Wi-Fi or cellular data networks. As a further option, data transmission and communication to the cart 10 could be in a wired fashion, such as through an ethernet cable, and hard wired into a location where the cart 10 is being utilized. In the case where wireless communication is involved, typically such communications would be appropriately encrypted to provide required and/or beneficial levels of privacy and confidentiality.

With particular reference to FIGS. 1-3 and 6, details of the power supply 90 and wireless charging system 100 (as an option) are described, according to this example embodiment. While some portions of the cart 10 and accessories thereof can operate without power, most of the accessories and compartments associated with the cart 10 have varying degrees of electric power requirements. In one embodiment, the cart 10 is merely plugged into a wall outlet 103 when power is required. When the cart 10 is moved, the cart 10 is unplugged by removing the plug 96 from the outlet 103, and then the cart 10 is plugged into an outlet 103 at a separate location after movement of the cart 10.

Most preferably, however, a rechargeable battery 92 is provided onboard the cart 10. This battery 92 is shown at an interface thereof on the side surface 40 of the cart 10, but could be at a variety of different locations within the cart 10. For instance, and with reference to FIGS. 2 and 3, such a rechargeable battery 92 (and CPU and other processing hardware associated with the control system 200) could be conveniently located in a lower central portion of the cart between the wheels 132, 142 to avoid interfering with function of the wheels 132, 142 or compartments, and to have the weight of the battery 92 somewhat as ballast to keep the cart 10 from having any tendency to tip over. In one embodiment the battery 92 and/or other ballast weight can be movable relative to the cart 10. An accelerometer and other sensors (e.g. strain gauges) can monitor center of gravity of the cart and topple risk for the cart, and shift the battery 92 or other ballast to counteract such tipping risk. Alarms and/or lights can provide warnings as well, or as an alternative to active balancing. Wheel 132, 142 movement could also be used to mitigate tipping risks. As another option, drawer opening can simultaneously trigger ballast and/or battery 92 movement to counteract the weight shift associated with drawer opening.

By making the battery 92 rechargeable, it's not strictly necessary that the cart 10 always be plugged into a wall outlet 103. Most preferably, a cord 94 leading from the battery 92 to the plug 96 is retractable in nature with a spring loaded spool interposed along the retractable cord 94, so that excess slack in the retractable cord 94 is spooled up onto the spool and avoids potential for entanglement or a tripping hazard, and generally maintaining a neat appearance. A USB port 98 is also preferably provided on the side surface 40 which could provide power to the battery 92, but which typically is provided for output of power from the battery 92, such as to allow for charging of a smart phone or other accessories which can be charged from a USB port.

In one embodiment, depicted in particular in FIG. 2, a wireless charging system 100 avoids the requirement for plugging in the cart 10. This wireless charging system 100 includes two parts which work together for wireless power transfer to the cart 10 from the outlet 103. On the cart 10, a pivot 102 supports a telescoping arm 104 and elongation along arrows K and L can occur through motorized actuators or through other automated powered actuators, such as pneumatics, hydraulics, gears, etc. In this way, the receiver disk 106 can be positioned precisely were required to facilitate wireless charging through inductive coupling.

The outlet 103 in the wall or other stationary surface is fitted with a power transmitter 105. This power transmitter 105 includes a plug 106 which can plug into a receptacle of the outlet 103. The power transmitter 105 has a transmitter disk 109 at the distal end of an arm leading from the plug 107. This transmitter disk 109 and the receiver disk 106 each include electrically conductive coils therein. Through inductive coupling, power can be transmitted between circuits of the power transmitter 105 and circuits associated with the receiver disk 106 of the wireless charging system 100 on the cart 10.

In one embodiment, the cart 10 is programmed to seek its own power source when a level of charge within the rechargeable battery 92 of the power supply 90 drops below a threshold level. One or more outlets 103 within a residence would be fitted with a power transmitter 105. The cart 10 would utilize its own wheels 132, 142 and associated steering and locomotion systems to move the cart 10 close to a power transmitter 105. The pivot 102 and telescoping arm 104 (and optionally also pivoting front-to-rear) would then function as an actuator to move the receiver disk 106 to be precisely aligned with the transmitter disk 109. Power transfer could then proceed. While the power transmitter 105 is shown with its transmitter disk 109 directly adjacent to the outlet 103, in one embodiment, an electric line between the plug 107 of the power transmitter 105 and the transmitter disk 109 could be greater in distance, and potentially flexible, and the transmitter disk 109 could be configured so that it can be mounted to the wall at a location which is easily accessible by the receiver disk 106 when the cart 10 is positioned at one of its primary desired use locations, such as bedside or chair side (FIGS. 4 and 5). In this way, the cart 10 can conveniently access power while it is being beneficially used by user U in a bed B or sitting on a chair C. Note that the user U in such an embodiment would not need to be concerned about keeping the cart 10 powered, or trying to plug in an electric plug 96. Rather, the cart 10 would take care of navigation and interconnection to maintain its power supply. Such a system can be incorporated into other medical carts in addition to the cart 10 of this particular embodiment, provided the cart is located sufficiently near a power transmitter disk 109 and/or includes powered and steerable wheels. A vision system or other locator system can aid the cart 10 to provide inputs for cart 10 and/or receiver disk 106 positioning and alignment with the transmitter disk 109.

With particular reference to FIGS. 2 and 3, details of various compartments of the cart 10 and secure access control associated therewith are described, according to this example embodiment. In this embodiment, and to maintain the cart 10 with the appearance of regular furniture, such as a nightstand, doors 110 and/or drawers 120 are provided adjacent to the front surface 30, which are configured to appear as doors and/or drawers of such furniture. In this particular embodiment, two doors 110 are provided most distant from a side surface 40 adjacent to where the user U is present, and two drawers 120 are provided closer to the user U and the side surface 40. Generally, compartments associated with the doors 110 are accessed horizontally, while compartments within the drawers 120 are accessed from above.

The door is 110 includes handles 111 thereon to facilitate pivoting of the doors 110 (along arrow N of FIG. 3) between a closed orientation and an open orientation. While the doors 110 could be locked, in this embodiment the doors 110 are not locked. Sub-doors 112 are provided behind at least one of the doors 110 in one embodiment. Handles 113 can be provided on such sub-doors 112. Lock buttons 114 are provided on such sub-doors 112 (or other electronic locks) to restricted access to compartments behind the sub-doors 112 and contents therein. As another option, sub-drawers 115 can be located behind at least one of the doors 110. Such sub-drawers 115 include handles 116 and lock buttons 118 to restrict access to such drawer compartments. Generally, a sub-drawer 115 compartment is utilized if the space is most beneficially accessed from above when the sub-drawer 115 has been slid open. Sub-doors 112 are utilized when it is most preferable to access the compartment behind the sub-door 112 horizontally. Various compartments, or an accessory on the surface can include a weighing scale (such as to weigh food intake, medications, items suspected of being too heavy for the user to lift, etc.). A floor pad could be deployed, such as from a compartment which can be used to weigh the user, such as in support of a telemedicine session.

Examples of compartments which might benefit from sub-doors 112 could include warming compartments or chilled compartments, such as compartments which would keep IV bags warm, keep clothes warm, keep medication cool, keep food items cool, or keep food items cold. In one embodiment, compartments can be configured to both maintain an elevated temperature or a reduced temperature, and would generally include insulation and heat transfer structures to achieve a desired temperature, along with thermostat controls and other interconnections to facilitate operation of such hot or cold compartments behind sub-doors 112.

Examples of items which will benefit from being located within a sub-drawer 115 (or bin) could include items which might fall out of a compartment if not bounded on lateral sides, such as jewelry and other small precious objects, coins or medications. While the sub-drawers 115 are shown with locks 118 on the sub-drawer 115 itself, such locks could be provided on a lid associated with the drawer 115, so that the drawer 115 can be freely slid horizontally, but a compartment within the sub-drawer 115 cannot be opened unless a code is entered into such a lock.

With regard to the lock buttons 114, 118, such lock buttons 114, 118 are merely one form of a portion of a locking system. Such a locking system includes mechanical locks and/or electrical locks and access protocols. Most preferably, the locks are all at least partially electronic in nature and are configured so that locking and unlocking of various compartments, whether drawers or doors, sub-doors or sub-drawers, can occur remotely. As another option, the cart 10 can be configured so that control over different compartments can occur either from a remote location or at the location of the cart 10. As an option, locks can be "break away" to allow one time emergency access, but indicating clearly that access occurred.

In many embodiments, it will be desirable for different individuals to have control over access to different compartments. As an example, medications might be provided within a compartment which has access to the medication controlled by a medical professional at a remote location, or with control provided both by a medical professional at a remote location and the user U. In this way, medication cannot be accessed unless authorized personnel approve of such access, and then only by the user U. Such approval can be on a case by case basis, or can be timed, such as 2 o'clock, so that a user can only take medication when called for by a medication protocol. Other compartments might contain valuables of the user U or might contain restricted access items such as tobacco, alcoholic beverages, and other items which the user desires to keep secret or otherwise maintain control over. Such compartments could have their locks configured to give control over access to the user U. Such control could be through entering a code into the lock buttons 114, 118. More preferably, such access would be provided through the tablet T or otherwise through sensors on the cart 10, such as biometric sensors (retina scan, finger print, facial recognition, etc.) which verify the authenticity of the user U and authorization to access certain compartments. Some compartments would not allow for general free access, but either remote authorized individuals or the user U can gain access. Other compartments could be freely accessible by anyone having access to the location where the cart 10 is located.

One example of use of the cart 10 which would be facilitated by the cart 10 and the associated doors 110 and drawers 120, and compartments associated therewith would be a telemedicine visit. A telemedicine visit would occur between the user U and a medical professional at a remote location. Video and audio for the session would typically be provided through the tablet T. Assessment of condition of the patient can be made visually and audibly by the medical professional communicating with the user U, as well as through sensors such as pulse/oxygen sensors, blood pressure sensors, temperature sensors, blood glucose sensors, etc. which can be built into the cart 10 or provided separately and communicate with the tablet T and/or the cart 10.

Based on the assessment of the medical professional, the medical professional might determine that it would be beneficial for the user U to access and take a particular medication orally. Various compartments within the cart 10 can be pre-loaded with various appropriate medications, and with all of the medication locked within these compartments. The medical professional could then remotely send a signal to the cart 10, causing appropriate compartments within the cart 10 to be unlocked so that the user U can access the appropriate medications. In one embodiment, a compartment might contain multiple doses of a particular medication, but in a manner which only allows one dose of the medication to be accessed and other doses of the medication to remain locked away. In this way, the user U cannot accidentally overdose and refilling of the compartments does not need to occur as often. The control system 200 can track that the unlocked compartment(s) were in fact opened, as a medication compliance/adherence tool. Various compartments can contain items for specific therapies, such as deep vein thrombosis therapy (DVT) and concealed when not in use.

Figure 7:
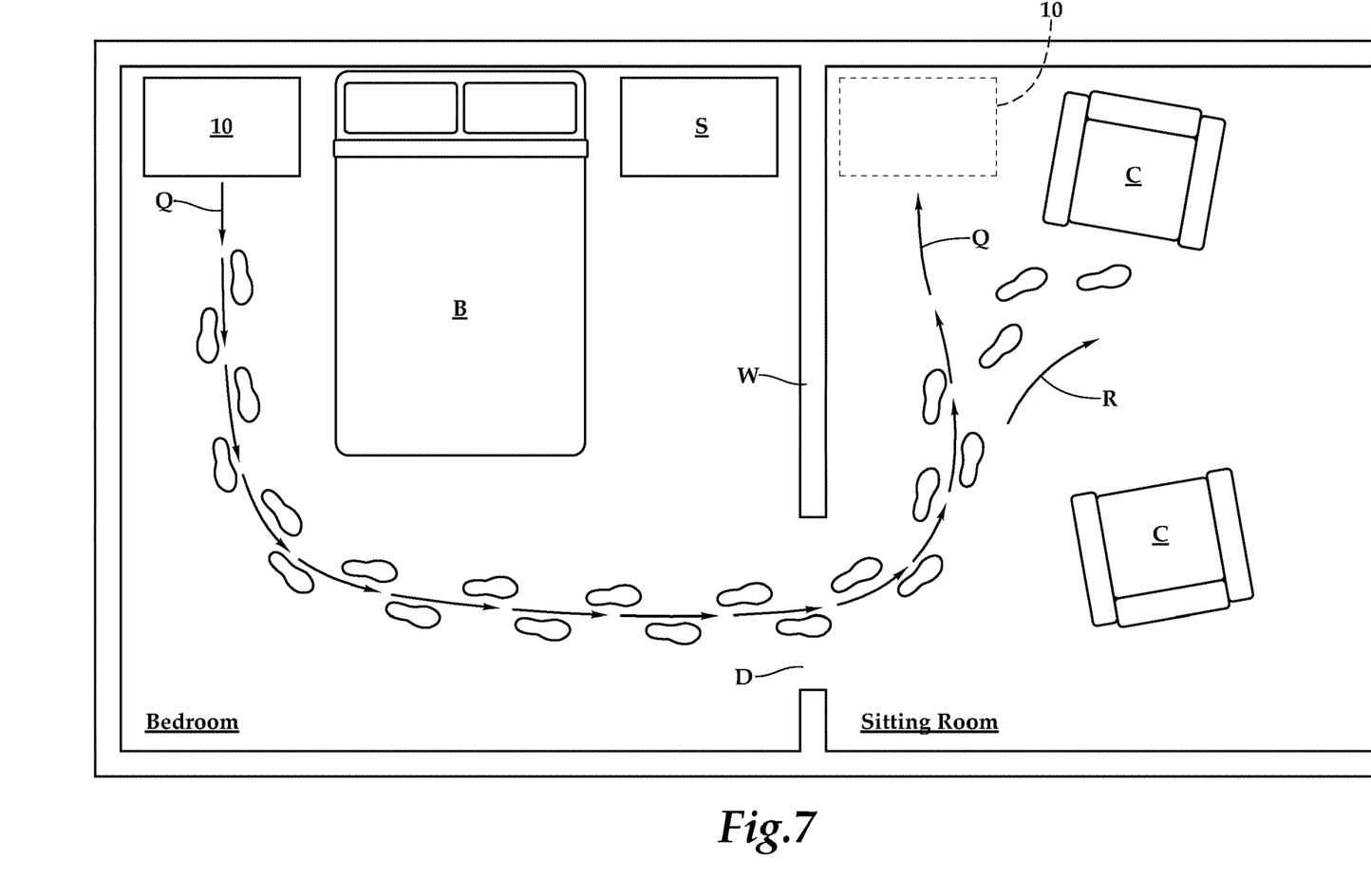
FIG. 7 is a top plan view of a residential area including a bedroom and sitting room, and showing how a user and the cart can navigate between a bedside location and a chair side location, according to one embodiment of the invention.

With particular reference to FIGS. 2 and 3, as well as FIGS. 4, 5 and 7, details of movement of the cart 10, either manually or in an automated fashion, are described according to this example embodiment. Motion of the cart 10 upon the wheels 132, 142 is controlled by a drive wheel assembly 130, a wheel steer assembly 140 and a wheel lift assembly 150. In a particular disclosed embodiment, two left side wheels are driven by the drive wheel assembly 130 and two right side wheels 142 are turned by the steering wheel assembly 140, and all of the wheels 132, 142 have elevation controlled by the wheel lift assembly 150. In alternative embodiments, four wheel drive and/or four wheel steering could be provided. Also, in alternative embodiments the wheel lift assembly 150 could be replaced with leg 58 extension/retraction, discussed in detail above.

The drive wheel assembly 130 causes the wheels 132 (one near the front surface 30 and one near a rear surface opposite the front surface 30, and both of these wheels 132 adjacent to a side surface opposite the side surface 40) to rotate (along arrow I of FIG. 2) and move the cart 10 upon the wheels 132, 142. In this embodiment, the wheels 132 are supported upon a hub 134 suspended at a lower end of forks 136. A drive motor 138 is provided as a friction motor directly transmitting torque (along arrow H of FIG. 2) from the drive motor 138 to tread on the wheel 132. As an alternative, a gear could be provided inboard or outboard of a tread of the wheel 132 which gear would be engaged by a spur gear on the drive motor 138 for gear drive of the wheel 132.

In one embodiment, only one of the left side wheels 132 is driven, but typically at least these two wheels 132 are both driven, and optionally all four wheels are driven. Various different types of wheels 132 could be provided. If the wheels 132 are visible, it is more desirable that they have a pleasing aesthetic appearance. If the wheels 132 are fully concealed, their configuration can be dictated more by optimizing function. The wheels 132 are shown with a relatively large diameter, which can assist in climbing over thresholds in doorways D, such as in a wall W between rooms (FIG. 7) and otherwise to navigate upon carpet or transitions between carpet and tile or other hardwood surfaces. In other environments with harder floors, smaller powered wheels 132 can be provided.

The powered wheels 132 are controlled by the control system 200 associated with the cart 10. As one option, a remote control input device can be controlled by user, either the user U or a remote authorized cart 10 driver. The cart 10 would then be driven according to the controls provided by the operator. In other embodiments, power to the wheels 132 can be automated, with the cart 10 programed to follow the user U, or move to a location where power can be accessed, or to move to a pre-programmed location following instructions provided by the user or a time schedule, or in anticipation of needs of the user U.

The steered wheel assembly 140 provides for control of steering of at least the wheels 142 associated with the steered wheel assembly 140. While in this embodiment only two wheels 142 are steered, most probably all four wheels are steered, so that the cart 10 can be most conveniently navigated in tight spaces, such as adjacent to a bed B in a bedroom environment. Four wheel steering would also more readily allow the cart 10 to move up close to a wall in which an outlet 103 is located, such as to facilitate wireless charging, as described in detail above, and to generally allow the cart 10 to be positioned adjacent to a wall in the manner that furniture is typically positioned.

The steered wheel assembly 140 includes the wheel 142 supported upon a rotating hub 144 at a lower end of angled forks 146. A steering control 148 and forks interface 149 act together to cause the angle forks 146 to rotate about a vertical axis. In particular, the steering control 148 can be in the form of an electric motor with an output spur gear. The forks interface 149 can include teeth which engage with this spur gear to cause the angled forks 146 to revolve about a centerline of this spur gear associated with the steering control 148. By making the angled fork 146 interface 149 have excess height, it can maintain engagement with the spur gear of the steering control 148 at various different elevations therebetween. Most importantly, the interface 149 remains engaged when in a lower position (along arrow G of FIG. 2) so that rotation of the steering control 148 spur gear (along arrow J of FIG. 2) will cause the entire angled forks 146 and wheel 142 to rotate and steer the cart 10 as desired. A motor associated with the steering control 148 would be coupled to the control system 200 so that steering control of the cart 10 can occur by an operator either located adjacent to the cart 10 (such as the user U) or an operator at a remote location. As an alternative, software programming associated with the control system can cause cart 10 movement and steering, such as to cause the cart 10 to move close enough to a wireless charging transmitter disk 109 to be able to access power wirelessly for the cart 10, and without requiring an operator to steer the cart into position for charging.

The wheel lift assembly 150 is similar for each of the wheels 132, 142. As one example, a worm gear 152 is rotatably supported below an output shaft 156. A rack gear 154 is provided upon the forks 136, 146. As the worm gear 152 rotates (along arrow F of FIGS. 2 and 3), the worm gear 152 causes the associated forks 136, 146 to be elevated or lowered relative to the output shaft 156 (along arrow G of FIG. 2). In this way, the wheels 132, 142 can be lifted up so that the legs 50 come into contact with the ground through the feet 54 and the cart 10 rest upon the legs 50, or can have the wheels 132, 142 lowered until the cart 10 can roll upon the wheels 132, 142. The wheel lift assembly 150 and/or height adjustment of the legs 50 or other system can also be used to allow the cart to climb up or down stairs.

Other accessories which can be provided upon the cart 10 include a lamp 170 such as the reading lamp shown in FIGS. 1, 4 and 5, which is preferably pivotable to provide light as desired for viewing and/or reading of various items by the user U or others. Lighting can also be strategically placed within compartments, which turn on when the compartments are opened to visualize contents. This lamp 170 is strategically located to remain out of position unless needed, such as between the IV pole 60 and the bottle support bracket 72 of the oxygen system 70.

An aroma generator 180 (optionally also or separately being a room humidifier) and water feature 190 can be provided, such as on the top surface 20 of the cart 10. The aroma generator 180 and water feature 190 assist in providing a calming and desirable ambience as well as for sound and aroma therapy (optionally including marijuana and other vaporizer based therapies). The oxygen mask 76 can optionally be coupled to the aroma generator 180 to more directly provide vapor therapy to a user U. Other accessories could similarly be built into the cart 10 or merely placed upon the top surface 20 or otherwise attached to the cart 10 for utilization therewith.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A cart, comprising:
   a frame;
   legs at four corners of said frame extending down to feet;
   wheels on a lower portion of said frame and supporting said frame above an underlying surface;
   said wheels movable vertically relative to said feet so that a lowest portion of the cart can be converted and the cart can rest either upon said feet of the legs or upon said wheels;
   at least one compartment supported by said frame, said compartment having an open configuration where contents of said compartment can be accessed and a locked configuration where contents of said compartment cannot be accessed without unlocking said compartment;
   a display coupled to the cart in a fixed or removable fashion;
   an audio speaker coupled to the cart;
   a microphone coupled to the cart;
   wherein said at least one compartment includes a pivoting door pivotable relative to said frame of the cart;
   wherein said pivoting door is an outer door and a sub door is located behind said outer door, said sub door having a lock thereon having said locked configuration where contents of said compartment cannot be accessed without unlocking said compartment and said outer door not having a lock thereon, said outer door concealing said sub door from being viewable except when said outer door is at least partially open; and
   wherein said sub door pivots about a vertical axis and wherein said outer door pivots about a vertical axis.

2. The cart of claim 1 wherein both said outer door and said sub door are pivoted directly to said frame of the cart, without any motion between said doors and said frame other than pivoting of said doors relative to said frame.

3. The cart of claim 2 wherein the cart has a configuration which causes said cart to appear as a nightstand when appearing to be resting on said legs, including said legs extending down beyond a front surface of the cart, with said legs terminating at lowermost portions thereof with feet, said feet configured to be at an elevation above at least portions of said wheels for a least one vertical position of said wheels, such that said legs and feet have an appearance of a nightstand but actually do not contact the ground and the cart can roll with the function of a cart while having an appearance of a nightstand.

4. The cart of claim 3 wherein said cart has major surfaces including a top surface, front surface and at least one side surface which are each mutually perpendicular to each other, giving the cart a generally orthorhombic appearance with said front surface and said at least one side surface oriented within vertical planes and said top surface oriented within a horizontal plane.

5. The cart of claim 4 wherein said at least one compartment is accessible through said front surface, with said outer door forming a portion of said front surface and with said outer door pivoted about a vertical axis by a hinge for accessing of said compartment through said sub door and through said front surface of said cart, when said sub door is unlocked and both said outer door and said sub door are open.

6. The cart of claim 5 wherein at least two compartments are accessible through said front surface through two separate outer doors, each said outer door pivotably attached to said front surface through separate hinges, and with each of said at least two compartments including separate lockable sub doors behind said two separate outer doors, said outer doors each configured to be wider than they are tall and with a separate handle on an exterior of each of said outer doors and spaced from said hinges, said handles for grasping of said outer doors and applying a torque to said outer doors to pivot said outer doors about said hinges and reveal said sub doors located behind said outer doors, for accessing of said compartments when said sub doors are unlocked.

* * * * *